(12) United States Patent
Ichino

(10) Patent No.: US 6,468,554 B1
(45) Date of Patent: Oct. 22, 2002

(54) SENSORIALLY ACTIVE SUBSTANCE EMBEDDED IN PLASTIC

(76) Inventor: Ted Ichino, 203 N. Lucia Ave. #4, Redondo Beach, CA (US) 90277

(*) Notice: Subject to any disclaimer, the term of this patent is extended or adjusted under 35 U.S.C. 154(b) by 0 days.

(21) Appl. No.: 09/247,953

(22) Filed: Feb. 11, 1999

Related U.S. Application Data

(63) Continuation-in-part of application No. 08/668,616, filed on Jun. 7, 1994.

(51) Int. Cl.$^7$ ................................................ A01N 25/10
(52) U.S. Cl. ...................... 424/406; 424/405; 424/409; 424/411; 514/555; 514/920
(58) Field of Search .................. 424/405–407, 424/409, 84, 411, 78.09; 514/555, 920

(56) References Cited

U.S. PATENT DOCUMENTS

| | | | | |
|---|---|---|---|---|
| 3,269,902 A | * | 8/1966 | Goodhue et al. | 167/46 |
| 3,663,253 A | * | 5/1972 | Stone | 106/204 |
| 4,204,018 A | * | 5/1980 | Bernstein et al. | 428/246 |
| 4,542,162 A | * | 9/1985 | Rutherford et al. | 521/79 |
| 4,818,535 A | * | 4/1989 | Baines et al. | 464/407 |
| 5,322,862 A | * | 6/1994 | Kurata et al. | 523/122 |

OTHER PUBLICATIONS

Merck—Denatonium Benzoate p. 328, 1968.*
Denatonium Benzoate C–Tech Corp. Brochure, 1990.*

* cited by examiner

Primary Examiner—Neil S. Levy

(57) ABSTRACT

Denatonium benzoate (Bitrex™) dissolves in molten flexible polyvinyl chloride, imparting a bitter flavor to the plastic which discourages rats from gnawing on it. Denatonium benzoate can in all likelihood be added to polymers other than polyvinyl chloride (e.g., polyurethane or polyethylene) either directly or by first dissolving the denatonium benzoate in an organic solvent which is miscible with the chosen polymer and then mixing this solution of organic solvent and denatonium benzoate into a molten solution of the chosen polymer.

2 Claims, 2 Drawing Sheets

SENSORIALLY ACTIVE SUBSTANCE EMBEDDED IN PLASTIC

This application is a continuation-in-part of application Ser. No. 08/668,616, filed on Jun. 7, 1994.

BACKGROUND—Field of Invention

This invention relates to bitter-tasting substances embedded in a substrate, by which means said substrate is provided a measure of protection against gnawing damage; and particularly to denatonium benzoate (Bitrex™) embedded in a polymer matrix.

BACKGROUND—Description of Prior Art

Gnawing damage to plastic cable housing caused by rodents is a multimillion dollar problem; squirrels gnawing on exposed plastic cables cause multiple power outages around the country, while prairie dogs wreak havoc on buried cable in many parts of the Mid West. Heretofore, the Prior Art has attempted to prevent such gnawing damage by creating microcapsules filled with a capsaicine compound within a resin molding composition (Kurata, et. al., U.S. Pat. No. 5,456, 916). This entails the use of an insoluble dispersing medium (usually water); often an acid binding agent is also needed. However, creating microcapsules ensures that, the active agent will not be evenly distributed throughout the substrate. In particular, a solution or suspension of capsaicine in a resin matrix will not be created. There are disadvantages to forming microcapsules. Bubbles and inclusions are well known to cause stress concentrations which weaken the material in which they occur; microcapsules would similarly be expected to weaken the treated resins. The method disclosed for creating microcapsules would appear to require substantial modifications to current manufacturing apparatus; this is a substantial drawback. Further, the size of the microcapsules places a limit on how thin a sheet of resin or plastic can be manufactured, and the solvent could prove to be a painful eye irritant in the event of leakage. The creation of microcapsules is not necessary if the aversive agent is intense enough: a compound such as Bitrex™ (denatonium benzoate), the bitterest substance known, is powerful enough to repel rodents without the need to resort to the "strength in numbers" approach afforded by microcapsules. Embedding microcapsules in a resin matrix is an interesting approach, but has many drawbacks which are avoided by the present invention.

Harding (U.S. Pat. No. 4,795,637) discloses how to make a rodent-repellent powder. This powder offends the rodent's sense of smell rather than its sense of taste; additionally the scent is not directly mixed into a specific substrate which is to be protected, but instead is applied to a general area.

An Internet entry (http://www.waite.adelaide.edu.au/~pclarke/science/bitter_the_most) of Nov. 23, 1996 alludes to denatonium benzoate (Bitrex™) being added to nail-polish, which is then painted on the fingernails of young children to prevent them from chewing their fingernails. Although this application might seem to superficially resemble the present invention, it in no way anticipates it. The present invention seeks to directly imbue a substrate with sensorially-active properties (for instance, the addition of Bitrex™ to plastic cable sheathing to prevent rodents from chewing on the sheath). Bitrex™ is not added to nail-polish to protect the nail-polish. Instead, the Bitrex™ in the nail-polish protects whatever the polish is painted upon.

This difference becomes clear when viewed from the perspective of protected substrates. In the cable sheathing example, the substrate to be protected is the plastic sheathing itself. In the nail-polish example the substrate to be protected is the fingernail, but the Bitrex™ has not been added directly to the fingernail. Instead, it has been added to nail polish, which is then painted over the fingernail. The equivalent in the cable sheathing example would be to spray a bitter-tasting compound onto the exterior of the cable sheath, rather than impregnating the plastic itself with this bitter-tasting compound.

The required physical properties of the substrates also differ. A "nail-polish-type" substrate must be either liquid or have adhesive qualities, or both. In contrast, a cable sheath cannot be liquid; nor should it possess adhesive qualities. It must provide structural integrity, precluding it from being a liquid; and must be easy to work with, precluding it from being sticky. Polymers like polyvinyl chloride and polyethylene, while excellent candidates for cable sheath substrates, would not be suitable materials for "nail-polish-type" substrates.

The present invention will not, in all likelihood, produce skin or eye irritation. Studies have shown Bitrex™ to be non-irritating to the skin even in fairly high concentrations. If skin irritation were to become an issue, the sheath can be co-extruded with the Bitrex™-treated plastic contained inside of a normal plastic outer skin. Co-extrusion, while expensive, will greatly mitigate, if not completely eliminate, any objectionable side effects. Thorough rinsing should eliminate any residual traces of bitter substance which might be picked up on the hands and transferred to the mouth of a person handling plastic treated with Bitrex™; handling treated plastic should not cause unpleasant bitter tastes in the mouths of the handlers.

Objects and Advantages

Accordingly, besides the rodent-repelling objects and advantages described above, several objects and advantages of the present invention are:

Lamp cords made of Bitrex™-treated plastic which dissuade pets and young children from chewing on them Thin sheets of Bitrex™-treated plastic which can be wrapped around furniture legs to minimize gnawing damage due to pets Slipper soles made of Bitrex™-treated plastic which discourage gnawing by pets Electric cable sheaths made of Bitrex™-treated plastic which deter rodents from gnawing on the cable sheaths Optic fiber cable sheaths made of Bitrex™-treated plastic which deter rodents from gnawing on the cable sheaths Environmentally-friendly rodent damage control Energy savings, cost savings, and time savings due to greater cable longevity and the consequently reduced need to excavate and repair buried cables Greater system reliability due to reduced rodent damage to system components Coatings for above-ground power and telephone lines which protect against gnawing damage Sheathing which can be wrapped around tree trunks to afford a measure of protection against beavers Plastic exterminator suits which discourage rodent bites Note that the substrate need not be plastic; it could be fiberglass or styrofoam or any material which can effectively retain the flavoring agent. Protection is not restricted to guarding against rodent gnawing damage; any animal which is averse to bitterness can be deterred from chewing on the treated substrate. The bitter agent is not restricted to Bitrex™; other bitter substances such as quassin or sucrose octa-acetate could be used instead. Since Bitrex™ readily dissolves in polyvinyl chloride, it can, in all likelihood, be added in the same step in which color is added—or even added in lieu of color. This has the obvious advantage of not requiring a change to the production line or manufacturing process—keeping down production costs and allowing inexpensive trial batches to be made.

DRAWING FIGURES

FIG. 1 shows a cable sheathing which has been impregnated with a compound with a disagreeable taste. The compound has been dissolved in the substrate, and thus is uniformly distributed throughout the substrate. A bitter-tasting substance is in solution in the plastic 10: all particles have been dissolved by the plastic.

FIG. 2 shows a cable sheathing which has also been impregnated with a compound with a disagreeable taste. The compound has not been dissolved in the substrate, but rather has been uniformly distributed throughout the substrate as a suspension or an emulsion. A bitter-tasting is suspended in plastic as a colloid 20. 'X' represents a particle in colloidal suspension.

FIG. 3 shows a block diagram diagramatically depicting a way to disseminate the sensorially-active agent throughout a plastic matrix. A flavoring agent 30 from a reservoir filled with a bitter-tasting substance 60 is added to liquid plastic 50. A stirrer 40 ensures that the flavoring agent 30 is evenly dispersed throughout the molten plastic 50.

FIG. 4 shows a flavored cable sheath which has been co-extruded with an outer layer of ordinary plastic. The cable appears to be a normal plastic cable until its outer layer is breached. A layer of normal untreated plastic 70 encloses a layer of plastic that has been treated with a bitter-tasting substance 80.

BRIEF DESCRIPTION OF FIGS. 1 to 4

A typical embodiment of this invention is illustrated in FIG. 1. A compound having a disagreeable taste has been dissolved in the plastic comprising the sheath; if an animal chews on the plastic sheath, the unpleasant taste deters the animal from continuing to chew the sheath.

DESCRIPTION OF INVENTION

Figure 1:
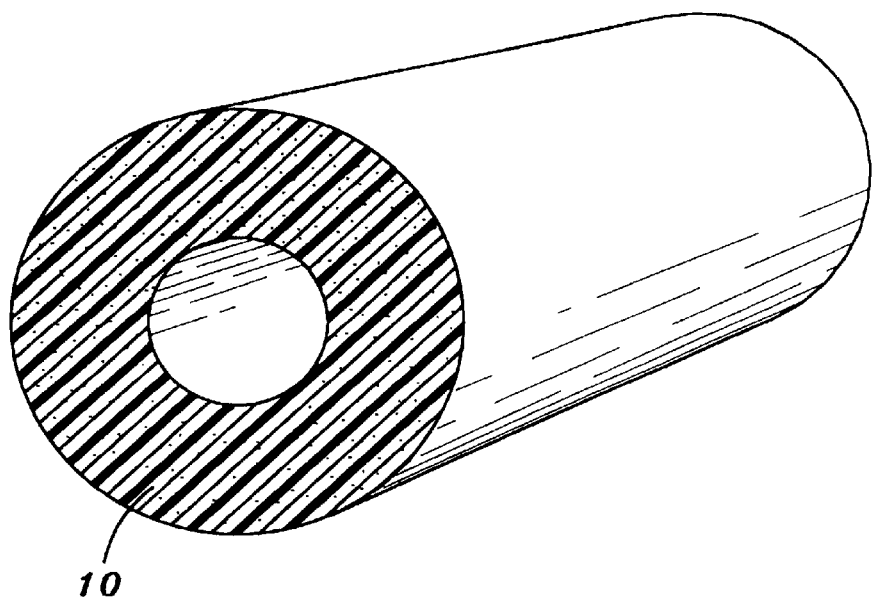
Figure 2:
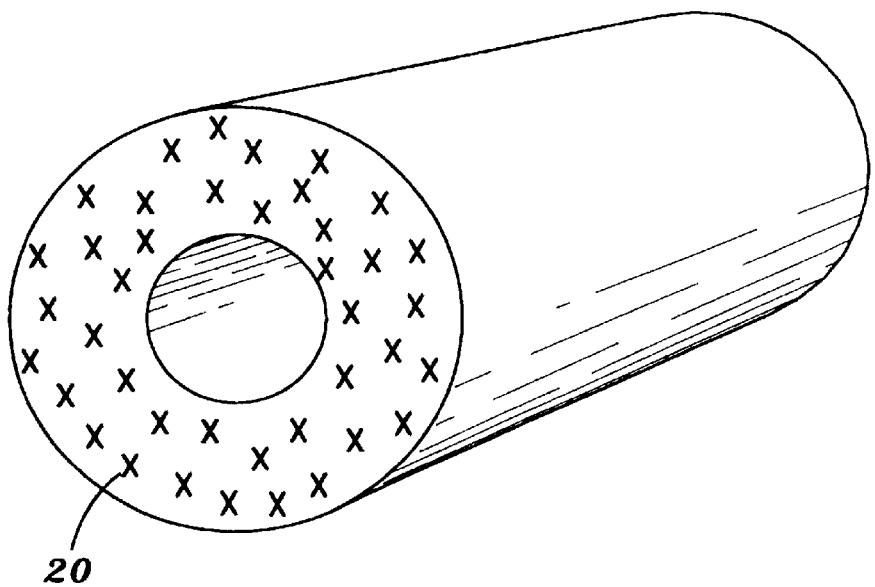
FIG. 2 shows a compound having a disagreeable taste which is not dissolved in the plastic but instead dispersed throughout the plastic as a suspension or an emulsion. Unexposed particles are preserved by the plastic matrix; if the sheath is buried in the ground, the flavoring agent will not leach out.
Figure 3:
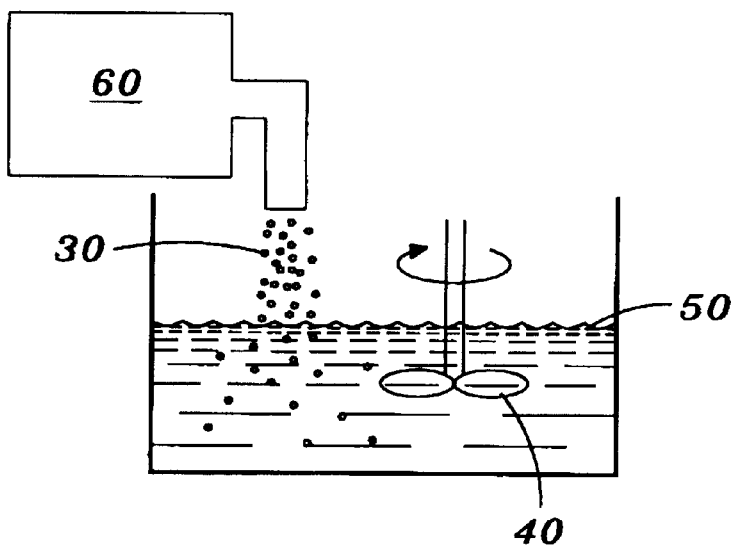
FIG. 3 depicts a possible means by which the sensorially-active substance is incorporated into the plastic matrix. The process depicted is well known to the art; for instance, color could be added to a clear plastic using a similar process.
Figure 4:
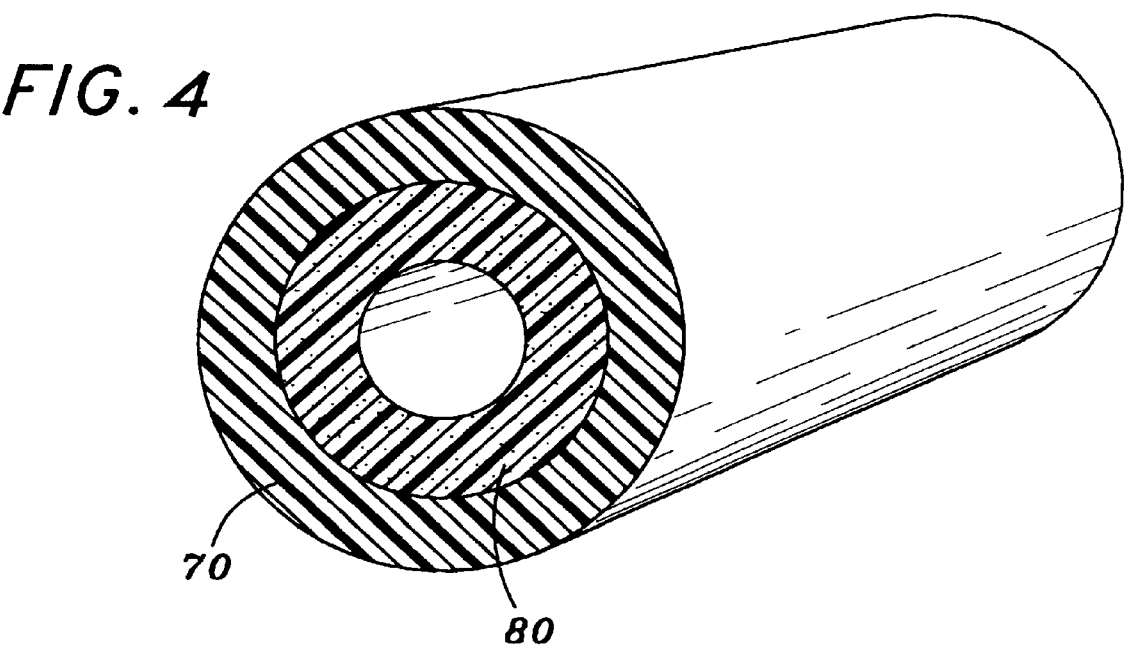
FIG. 4 shows a treated plastic sheath which has been co-extruded with normal plastic. The ordinary plastic forms a protective barrier against incidental contact with the treated material of the inner sheath.

Denatonium benzoate readily dissolves in molten polyvinyl chloride (PVC). Adding approximately 0.2 grams of denatonium benzoate to 100 grams of clear flexible PVC yields a clear, brownish plastic. This concentration of denatonium benzoate does not deter rats from gnawing and eating the PVC, but does have a pronounced soporific effect on rats which ingest the treated PVC. Adding approximately 2.5 grams of denatonium benzoate to 100 grams of clear flexible PVC yields a dark red plastic with an acrid odor. This concentration of denatonium benzoate has proven to be quite effective in discouraging rats from gnawing on the plastic, even when the sample was thoroughly washed to remove any latent denatonium benzoate crystals from its surface. It is probable that this concentration represents a practical maximum; past this level, the PVC changes consistency, becoming sticky, and an objectionable bitter flavor pervades the air. Upon cooling, free crystals of denatonium benzoate reside on the surface of the PVC. These crystals are invisible to the naked eye, but can readily be tasted. Precipitation of crystals typically indicates a saturated or supersaturated solution, and is further evidence that the maximum solubility of denatonium benzoate in PVC has been reached. A layer of normal untreated plastic 70 encloses a layer of plastic that has been treated with a bitter-tasting substance 80.

It is quite possible that lower concentrations of denatonium benzoate will provide adequate protection against gnawing damage; this needs further investigation. Only flexible PVC was used in the experiments, and the agent responsible for dissolving the denatonium benzoate was not determined. Denatonium benzoate may be directly soluble in PVC; on the other hand, it may be dissolved by the plasticizers contained in flexible PVC.

Denatonium benzoate is the preferred additive, as a large body of research attests to its safety. It has been officially approved by the EPA, OSHA, and the USDA for a variety of applications; it has low toxicity and does not irritate the skin at concentrations of 0.05%. The levels encountered in handling denatonium-treated PVC should be far lower than this, since nearly all of the denatonium benzoate will be embedded in plastic, and any crystals residing on the outside of the PVC will readily wash off in water. Other additives certainly exist, but denatonium benzoate appears to be the most promising candidate. Denatonium benzoate can be added to plastic in the same step when color is added; there should be no need to modify existing manufacturing apparatus.

Plastics other than PVC are good candidates for treatment with denatonium benzoate. As discussed above, if denatonium benzoate is being dissolved by the plasticizers contained in flexible PVC, any plastic containing similar plasticizers would be treatable. If the denatonium benzoate is being dissolved by the PVC, there is a chance that it will also dissolve in other plastics, e.g., polyurethane or polyethylene. If the denatonium benzoate is not directly soluble in a given plastic, it can be introduced by first dissolving it in a common solvent, e.g., chloroform. This solution can then be mixed into the plastic, yielding a solution, a suspension, or an emulsion of denatonium benzoate in the plastic.

SUMMARY, RAMIFICATIONS, AND SCOPE

Accordingly, the reader will see that this invention, by defining a new class of additives to plastic, has the potential to greatly extend the lifetime of power lines, phone lines, or indeed anything enclosed in a plastic sheath.

Although the description above contains many specificities, these should not be construed as limiting the scope of the invention but as merely providing illustrations of some of the presently preferred embodiments of this invention. For example, denatonium benzoate could be replaced with sucrose octa-acetate or quassin, which are quite bitter and could serve as flavoring agents.

Plastic need not be the substrate material; other candidate materials include fiberglass and styrofoam. Any material which can hold a sensorially-active ingredient is potentially a candidate substrate. Plastic may be the most ubiquitous medium, but it is by no means the sole medium.

The sensorially-active agent need not be soluble in the substrate. Bitrex™, being nearly insoluble in ether, would not be expected to dissolve in molten plastic. As it turns out, it actually is soluble in PVC, but even if it were not soluble, its lack of solubility would not exclude Bitrex™ from the candidate substances suitable to impart a foul taste to a substrate material. A suspension of Bitrex™ in plastic is likely to be as effective a deterrent as an alternate substance (such as quassin) dissolved in the plastic. The sensorially-active agent need not be uniformly distributed throughout the substrate for it to be effective. Bitrex™ is readily soluble in organic solvents such as benzene and chloroform; if it refuses to dissolve directly into the substrate there is a good chance of introducing it into the substrate by first dissolving it in a solvent which is miscible with the substrate. Note that this method does not seek to create microcapsules; it merely seeks to distribute the Bitrex™ evenly throughout the substrate. This distribution can take several forms; it can be a solution (Bitrex™ dissolved in plastic), a suspension (fine particles of Bitrex™ suspended in plastic), or an emulsion (larger particles of Bitrex™ suspended in plastic). Particles of Bitrex™ suspended in plastic might be an even more effective deterrent than a solution of Bitrex™ in the same plastic; a particle would presumably have a more concentrated taste than the same amount of Bitrex™ spread uniformly through the plastic. Again, please note that this method seeks to create a colloidal suspension rather than a collection of microcapsules.

Thus the scope of the invention should be determined by the claims which follow and their legal equivalents, rather than by the examples given.

I claim:

1. A method of imparting a sensorially active substrate in a cylindrically shaped plastic sheath comprising the steps of:

a. Heating a plastic material to a molten state;

b. Imparting a bitter taste to said molten plastic material by distributing a measured amount of denatonium benzoate comprising no more than 2.5% of the total weight of said plastic material into said molten plastic material, said measured amount being effective to protect an object fashioned from said molten plastic material from damage due to chewing animals;

c. Coaxially extruding the plastic to form a cylindrical sheath, thereby protecting the constituent of the sheath from damage caused by chewing animals.

2. A process for imparting a sensorially active substrate in a plastic matrix which comprises:

a. Heating a plastic material to a molten state;

b. Distributing a measured amount of denatonium benzoate comprising no more than 2.5% of the total weight of said plastic material throughout the plastic matrix formed by melting said plastic material, imparting a bitter taste to said plastic matrix effective to provide protection from damage due to chewing animals;

c. Extruding the plastic matrix to form a protective sheath, whereby the constituent of the sheath will be shielded from damage caused by chewing animals.

* * * * *